United States Patent
Freud et al.

(12) 
(10) Patent No.: US 6,396,979 B1
(45) Date of Patent: May 28, 2002

(54) OPTICAL WAVEGUIDE PROBE HAVING VARIABLE GAP FOCUSING

(75) Inventors: Paul J. Freud, Furlong; Michael N. Trainer, Telford, both of PA (US)

(73) Assignee: Microtrac, Inc., Montgomeryville, PA (US)

( * ) Notice: Subject to any disclaimer, the term of this patent is extended or adjusted under 35 U.S.C. 154(b) by 0 days.

(21) Appl. No.: 09/349,813

(22) Filed: Jul. 9, 1999

(51) Int. Cl.$^7$ .................................................. G02B 6/32
(52) U.S. Cl. ............................. 385/34; 385/33; 385/15; 385/93
(58) Field of Search ............................. 385/34–35, 74, 385/90–93; 356/336

(56) References Cited

U.S. PATENT DOCUMENTS

| | | | |
|---|---|---|---|
| 4,865,029 A | * 9/1989 | Pankratov et al. | 128/303.1 |
| 4,871,251 A | * 10/1989 | Preikschat et al. | 356/336 |
| 5,094,526 A | * 3/1992 | Freud et al. | 356/28.5 |
| 5,684,644 A | * 11/1997 | Spears et al. | 385/34 |

* cited by examiner

*Primary Examiner*—Rodney Bovernick
*Assistant Examiner*—Juliana K. Kang

(74) *Attorney, Agent, or Firm*—Wood, Herron & Evans, L.L.C.

(57) ABSTRACT

An adjustable focusing assembly for use with an optical probe includes a focusing element having a first and a second end mounted within a holder member. The holder member is secured to the optical probe with the focusing element optically coupled to the light images projecting from the light probe. A window having an inner and an outer surface is mounted on a body member with the window inner surface in a facing and spaced relationship to the focusing element second end. The body member further includes a cowled portion extending from the periphery of the body member on a side opposite the window, arranged to engage surfaces on the periphery of the holder member, thereby defining a cavity between the focusing element second end and the window inner surface. The body member is adjusted, increasing or alternatively decreasing the cavity until the light images from the focusing element second end are focused on the window outer surface. Upon establishment of the focus, the cowled portion is fixed to the holder member, fixing the focusing assembly to the optical probe. A second embodiment is also disclosed that alternatively locates the focusing element against the window inner surface forming the adjustable cavity between the focusing element and the optical probe. The body member is adjusted increasing or alternatively decreasing the cavity until the light images from the focusing element second end are focused on the window outer surface.

24 Claims, 3 Drawing Sheets

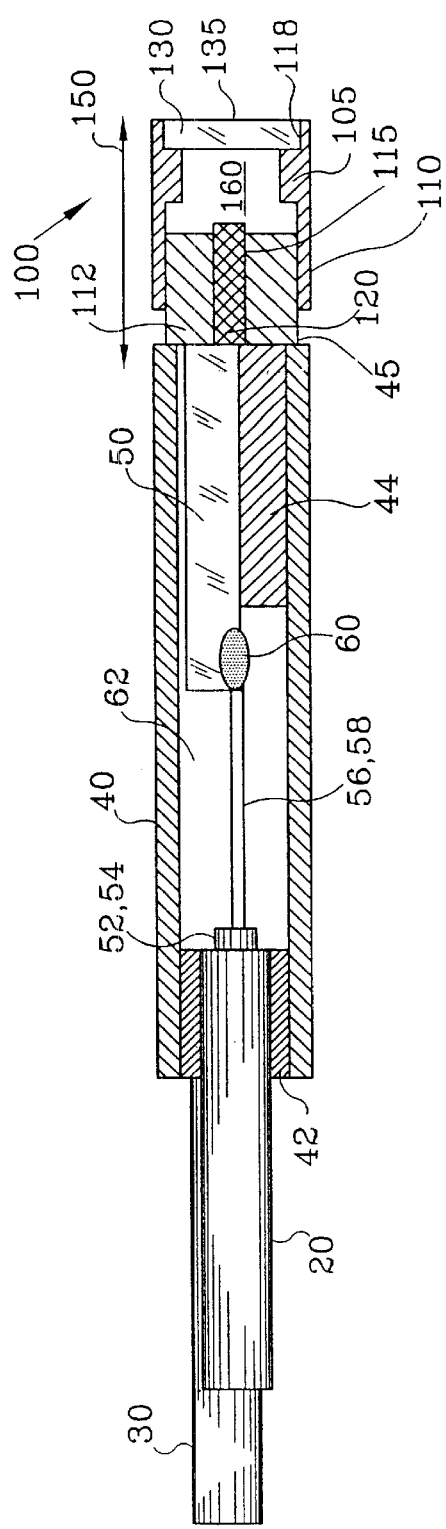
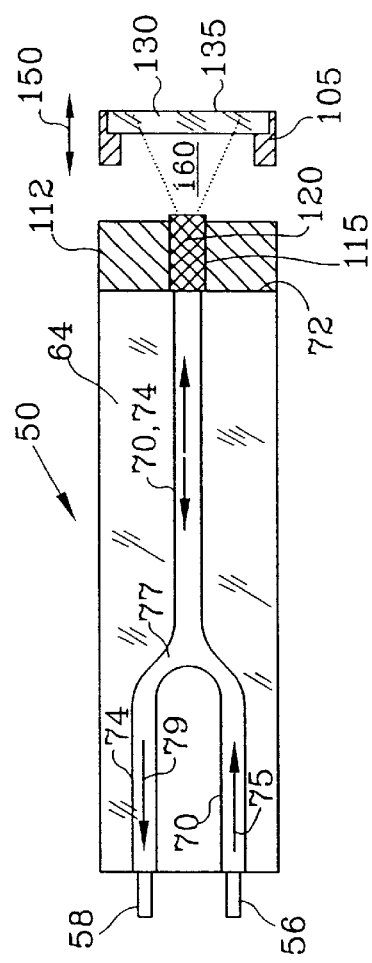
Fig. 3
Fig. 4

OPTICAL WAVEGUIDE PROBE HAVING VARIABLE GAP FOCUSING

BACKGROUND OF THE INVENTION

1. Field of the Invention

The present invention relates generally to the field of optical sensors used with apparatus for measuring the size and velocity of particles suspended in a fluid medium, and more specifically to an optical waveguide probe having variable gap focusing for transmitting light to and from the measurement zone.

2. Discussion of the Related Art

U.S. Pat. No. 5,094,532, issued Mar. 10, 1992, and entitled "Method and Apparatus for Measuring Small Particle Size Distribution", to Michael N. Trainer et al., and currently assigned to the assignee of the present invention, teaches a method and apparatus for measuring the size distribution of very small particles suspended in a fluid medium. The apparatus described includes a dynamic light scattering instrument having an optical coupler.

U.S. Pat. No. 5,094,526, issued Mar. 10, 1992, entitled "Integrated Optical Waveguide Doppler Velocimeter", to Freud et al., and currently also assigned to the assignee of the present invention, describes an optical apparatus that is used to practice the small particle size distribution measurement methods taught by U.S. Pat. No. 5,094,532. U.S. Pat. No. 5,094,526 describes an optical apparatus having a 2×1 optical waveguide splitter that is integral to a probe assembly that forms a part of the Doppler velocimeter. The integrated optical surface waveguide includes a first optical waveguide path that receives an incident beam of light from a light source on one end. The first waveguide path guides the incident beam to a second end that further includes an optical focusing element and a glass rod element permanently secured to the second end. The glass rod is immersed into the suspension medium containing the particles to be measured and conveys the beam to the suspension to irradiate the particle ensemble therein. A second optical waveguide path is optically coupled to the first waveguide path for receiving the scattered light from the particles as well as the non-scattered light Fresnel reflected from the face of the glass rod and guides both to the other end thereof. A detector receives the scattered and non-scattered light from the second waveguide and converts it to an electrical indicative of a Doppler frequency shift. The integrated optical waveguide has advantages over fiber optic couplers due to its more rugged nature, its reduced susceptibility to environmentally induced optical phase noise, its polarization stability and its favorable signal-to-noise ratio characteristics.

In the aforementioned construction the focusing element is secured to the first waveguide path by means of an index matching epoxy. The glass rod element is similarly fixed to the focusing element by means of a similar index matching epoxy. The epoxy is chosen to match as closely as possible the index of refraction of the first and second waveguides in order to minimize any reflection between interfacing surfaces.

This construction requires a great degree of precision in the assembly of the focusing element and glass rod to the waveguide. In order to gain the maximum benefit from the focusing element's advantages in increasing the field of view, the focusing element and glass rod must be sized to allow the focus of the beam to fall substantially on the face of the rod. Therefore, the design and assembly of these elements requires consideration to the size of the elements, gradient index of the focusing element, and the gap of the epoxy layers used in attaching the elements to each other and to the waveguide. Due to the fixed spatial relationships between the elements and the waveguide, a considerable degree of engineering effort, skill and time is required in the design and assembly of such an optical probe in order for it to provide optimal performance within its intended use.

Therefore, it is an object of the present invention to provide an optical waveguide probe with an optical focusing assembly that can be easily attached and manipulated in order to provide the optical probe with optimal performance characteristics without the need for consideration of the physical and operational factors of the focusing elements.

It is another object of the invention to provide a variable gap focusing structure for an optical waveguide probe that greatly reduces the complexity and precision of its manufacture and assembly.

BRIEF SUMMARY OF THE INVENTION

In accomplishing these and other objects, there has been provided, in accordance with the present invention, an adjustable focusing assembly for an optical waveguide probe. The optical probe includes a housing and an optical waveguide having a termination end for the emission and reception of light images mounted within the housing, with the termination end proximate a housing first end. The focusing assembly includes a focusing element having a first and a second end mounted within a holder member. The holder member is secured to the housing first end with the focusing element first end adjacent to, and optically coupled to, the optical waveguide termination end. A window having an inner and an outer surface is mounted on a body member with the window inner surface in a facing and spaced relationship to the focusing element's second end. The body member further includes a cowled portion extending from the periphery of the body member on a side opposite the window, arranged to engage surfaces on the periphery of the holder member, thereby defining a cavity between the focusing element second end and the window inner surface. The body member is adjusted increasing or alternatively decreasing the cavity until the light images from the focusing element second end are focused on the window outer surface. Upon establishment of the focus, the cowled portion is cemented to the holder member, fixing the focusing assembly to the optical probe. Alternatively, the cavity is filled with an epoxy cement having an index of refraction that closely matches the index of refraction of the optical waveguide. After adjustment of the body member to focus the light images on the window outer surface, the focusing assembly is fixed to the optical probe by curing the index matching epoxy.

A second embodiment for accomplishing the objects is also provided that includes a focusing assembly having a focusing element with a first and second end mounted within a body member. A window having an inner and an outer surface is mounted on the body member with the window inner surface resting against and in contact with the focusing element first end. The body member further includes a cowled portion extending from the periphery of the body member on a side opposite the window, arranged to engage the housing first end, thereby defining a cavity between the termination end and the focusing element second end. With the cowled portion mounted on the housing, the focusing element second end is in a spatial and axial alignment with the optical waveguide termination end. The body member is adjusted until the light images on the termination end are transferred to the focusing element and focused on the window outer surface. Upon establishment of the focus, the cowled portion is cemented to the housing, fixing the focusing assembly to the optical probe.

Alternatively, the cavity is filled with an epoxy cement having an index of refraction that closely matches the index of refraction of the optical waveguide. After adjustment of the body member to focus the light images on the window outer surface, the focusing assembly is fixed to the optical probe by curing the index matching epoxy.

BRIEF DESCRIPTION OF THE SEVERAL VIEWS OF THE DRAWINGS

The features and advantages of the present invention will be apparent from the following description of the preferred embodiments thereof, taken in conjunction with the sheets of drawings, in which:

FIG. 3 shows, in partial cross section, the prior art optical probe modified to accept and use to advantage the variable gap focusing assembly of the present invention;

FIG. 4 shows, in schematic form, an integrated optical waveguide and the variable gap focusing assembly of the present invention;

DETAILED DESCRIPTION OF THE INVENTION

Figure 1A:
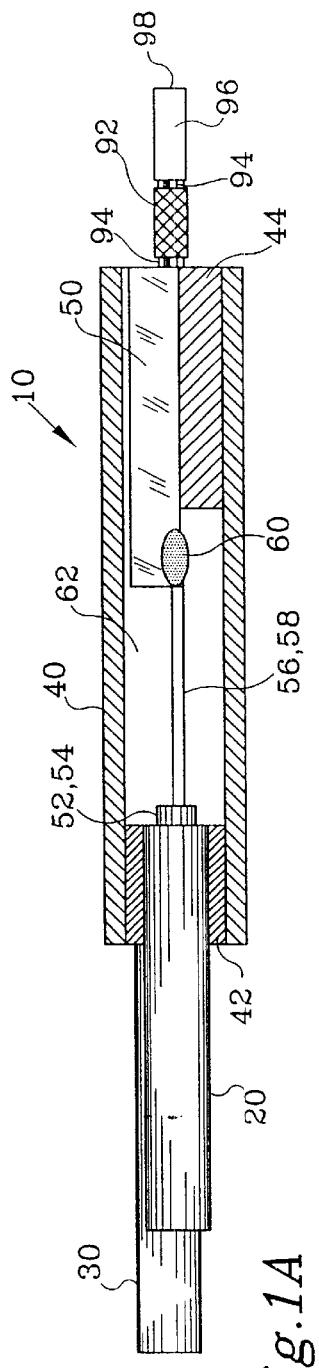
FIG. 1A shows, in partial cross section, the optical probe of the prior art Doppler velocimeter.
Figure 1B:
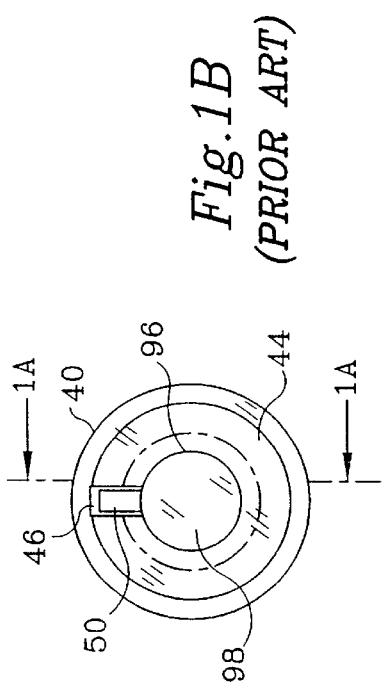
FIG. 1B shows a front end view of the optical probe of the prior art, shown in FIG. 1A.
Figure 2:
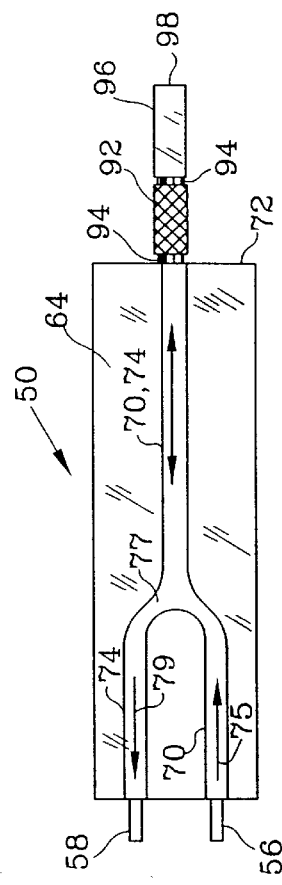
FIG. 2 shows, in schematic form, the integrated optical surface waveguide used by the prior art optical probe.

The present invention is intended to be used to advantage with a probe assembly of a Doppler velocimeter such as the Doppler velocimeter described in the aforementioned U.S. Pat. No. 5,094,526. Turning now to FIG. 1A and FIG. 1B of the included drawings, the prior art probe assembly will be described. The probe assembly 10 includes a fiber optic cable 20 adapted to receive an incident beam of light from a light source (not shown) and a fiber optic cable 30 for delivering a reflected light signal to a light detector (not shown). The probe assembly further includes a tubular housing 40, for protecting all delicate probe components. A suitable hard epoxy compound 42 bonds the ends of the fiber optic cables 20 and 30 within the housing 40 and provides a stress relief for cables 20 and 30. A support piece 44 is engaged in a force fitting relationship at the other end of housing 40 and includes a slot 46 extending the length thereof. An integrated optical surface waveguide 50 is supported within slot 46 by support member 44. As used herein, the term "integrated optical surface waveguide" is intended to mean one or more optical waveguide paths supported by and integral with a common substrate. A pair of tubes 52 and 54 extend from cables 20 and 30 respectively. In addition, optical fibers 56 and 58 contained within tubes 52 and 54 respectively are secured to the waveguide 50 by an epoxy cement 60. A silicon grease 62 fills the center of the housing 40 to protect the internal components from moisture. The waveguide 50 is shown in greater detail in FIG. 2 and includes a first optical waveguide path 70 connected to optical fiber 56, for receiving an incident beam of light at the end of path 70 abutting fiber 56. The path 70 serves to guide the incident beam to the other end 72 of waveguide 50. A second optical waveguide path 74 is optically coupled to path 70 at the portion abutting end 72 so that the said first and second waveguides form a Y-shaped configuration. The path 74 receives the scattered light from the moving particles and the Fresnel reflected light from the coupled ends of paths 70 and 74 and guides both the scattered and non-scattered light to the other end thereof and to optical fiber 58 for delivery to a light detector (not shown). The signal delivered from the light source along fiber 56 to path 70 travels in the direction of arrow 75 to end 72. The scattered signal from end 72 and the Fresnel reflected signal are split at junction 77 and delivered to path 74 in the direction of arrow 79. In order to increase the field of view and the sample scattering volume of the coupled portion of paths 70 and 74, a focusing element, or a Gradient Index (GRIN) focusing element, commonly known in the art as a GRIN rod, 92 is secured to the end 72 of the waveguide 50 through the use of an index matching epoxy 94. End 72 is typically positioned within a sample cell containing the scattering medium and the particles whose motion are to be measured. In order to protect the GRIN rod 92 and the waveguide 50 from the deleterious effects of a moisture-filled or caustic environment, a glass rod 96 is secured to the other end of the GRIN rod 92, also utilizing the index matching epoxy 94. The end 98 of the glass rod 96 is relied upon for the Fresnel reflection of the light beam delivered to end 72 by path 70. This assembly of a GRIN rod 92 and glass rod 96 permits a larger sampling volume to be viewed by the probe 10 and allows for a better averaging of particle statistics when samples containing large particles are measured. A better understanding of the probe 10 and its use in detecting the Doppler frequency shift of light scattered from particles suspended in a medium may be had by reference to U.S. Pat. No. 5,094,526, which is incorporated by herein by reference.

As mentioned earlier, however, this present construction of a GRIN rod 92 and glass rod 96 secured to the waveguide 50 via an index matching epoxy has certain disadvantageous. In order to gain the maximum benefit from the focusing element's advantages in increasing the field of view, the focusing element and glass rod must be sized to allow the focus of the beam to fall substantially on the face 98 of glass rod 96. Therefore, the design and assembly of these elements requires consideration to the size of the elements 92 and 96, the gradient index of the GRIN rod 92, and the gap of the epoxy layers 94 used in attaching the elements to each other and to the waveguide 50. Due to the fixed and permanent relationships between the elements 94 and 96 and the waveguide 50, a considerable degree of engineering effort, skill and time is required in the design and assembly of probe 10 in order for it to provide optimal performance.

In order to alleviate the aforementioned disadvantageous of the prior art probe 10, the present invention contemplates the use of a variable gap focusing assembly 100 that can be attached to probe 10 and manipulated in order to provide the probe 10 with optimal performance characteristics without the need for consideration of the physical and operational factors of the prior art elements 92, 94 and 96.

Turning now to FIG. 3 and FIG. 4 of the included drawings, the prior art probe 10 is shown modified to use the optical assembly 100 of the present invention. The optical assembly 100 is comprised of a cylindrical focusing element holder 112, constructed from the same material as housing 40, such as a stainless steel or plastic. Holder 112 further includes an opening 115, centrally located on holder 112 that traverses holder 112 from a first end to a second end. The focusing element holder 112 is attached to the housing 40 in any convenient manner presently known with opening 115 in axial alignment with the terminus of waveguide path 70, 74 located at end 72. Opening 115 is arranged to accept therein a focusing element or GRIN rod 120 that is retained within opening 115 by a thin layer of epoxy. With the GRIN rod 120 installed in opening 115, one end of the GRIN rod 120 rests adjacent to, and in contact with, end 72 of waveguide 50. A thin layer of epoxy is applied between end 72 and the GRIN rod 120 to fill any irregularities between the abutted surfaces that could degrade the quality of the optical coupling between them.

The optical assembly 100 further includes a cylindrical body member 105 having a recess 118 on one end of the body member 105 arranged to accept therein an optically transparent window 130. Window 130 is constructed from an optically transparent material such as glass or from a mineral composition such as sapphire. An opposite end of body member 105 includes a cowled portion formed from an integral cylindrical extension 110, extending from the outer periphery of body member 105. Extension 110 is constructed from the same material as body member 105 and surrounds and defines therebetween an interior space or cavity 160 that is adjacent window 130. Extension 110 is arranged to be slideably mounted onto the outer surface 45 of holder 112. With extension 110 engaged to surface 45, body member 105 is slideably displaceable in the direction shown by arrow 150. Upon engagement of extension 110 onto surface 45, body member 105 is displaced toward and/or away from the GRIN rod 120 until an optimum focus of the image from the GRIN rod is made on outer surface 135 of window 130. At this point the position of body member 105 to the probe 10 is fixed.

The body member 105 is fixed to the probe 10 by the application of a thin layer of epoxy cement or other fixing adhesive at the juncture of extension 110 and holder 112 surface 45. Reflections from the air/focusing element 120 surfaces will be at such angles that light not coupled initially into the focusing element 120 and entering the cavity 160 will not be coupled back into the return path of waveguide path 70, 74 and interfere with the main reflected signal from surface 135 of window 130.

Alternatively, cavity 160 can be filled with an epoxy cement that has an index of refraction matched to the waveguide 50. Cavity 160 is filled with an index matching epoxy that is initially uncured and liquid. Body member 105 is then displaced toward and/or away from GRIN rod 120, in the direction of arrow 150, until an optimum focus of the image from the GRIN rod 120 is made on outer surface 135 of window 130. Once the optimal focus is achieved, the body member 105 is retained in this position and the epoxy filling cavity 160 is cured, thereby, fixing assembly 100 at the focused position.

Figure 5:
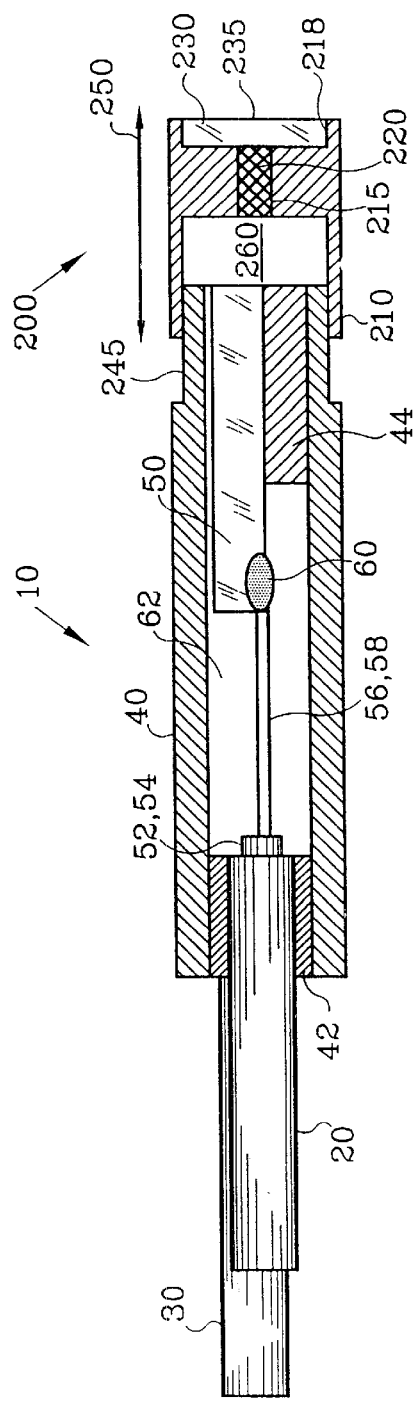
FIG. 5 shows, in partial cross section, the prior art optical probe modified to accept and use to advantage a second embodiment of the variable gap focusing assembly of the present invention.
Figure 6:
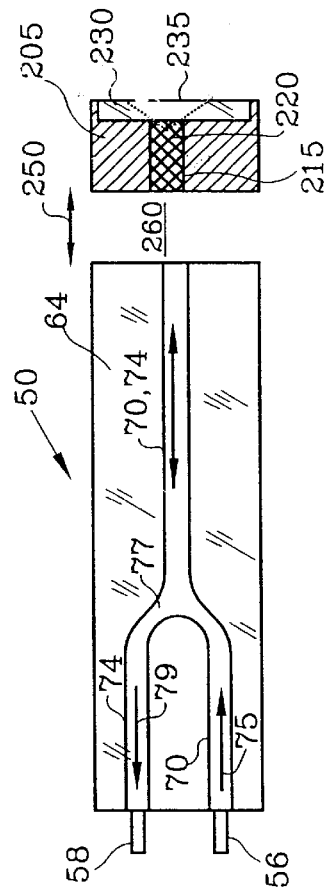
FIG. 6 shows, in schematic form, an integrated optical waveguide and the variable gap focusing assembly of the second embodiment of the present invention.

Turning now to FIG. 5 and FIG. 6 of the included drawings, a second embodiment for practicing the advantageous of the present invention is shown. Again the prior art probe 10 is shown modified to use an optical focusing assembly 200. The optical focusing assembly 200 is comprised of a cylindrical body member 205 constructed from the same material as housing 40, such as a stainless steel or plastic. A focusing element, or GRIN rod, 220 is housed within an opening 215 that longitudinally traverses body member 205. The element 220 is retained within opening 215 by a thin layer of epoxy. One end of the body 205 further includes a recess 218 arranged to accept therein an optically transparent window 230. Window 230 is constructed from an optically transparent material such as glass or from a mineral composition such as sapphire. A first end of the GRIN rod 220 abuts up to and rests against window 230. A thin layer of epoxy is also applied between the first end of GRIN rod 220 and window 230 to fill any irregularities between the abutted surfaces that could degrade the quality of the optical coupling between them.

An opposite end of body 205 includes a cowled portion formed from an integral cylindrical extension 210, extending from the outer periphery of body 205. Extension 210 is constructed from the same material as body 205 and surrounds and defines therebetween an interior space or cavity 260 that is adjacent to a second end of GRIN rod 220. Housing 40, proximate end 72 of the waveguide 50, is modified by providing a shoulder area having a receiving surface 245 located about the periphery of housing 40. Receiving surface 245 is sized to slideably accept thereon extension 210 of assembly 100. With extension 210 engaged to surface 45, the assembly 100 just described is slideably displaceable in the direction shown by arrow 250. Upon engagement of assembly 200 onto surface 45 of the probe, the assembly 200 is displaced toward and/or away from the waveguide 50 end 72 until an optimum focus of the image from the waveguide termination end 72 is made on outer surface 235 of window 230. At this point the position of assembly 200 to the probe 10 is fixed.

The assembly 200 is fixed to the probe 10 by the application of a thin layer of epoxy cement or other fixing adhesive at the juncture of extension 210 and surface 45 of housing 40. Reflections from the air/focusing element 220 surfaces will be at such angles that light not coupled initially into the focusing element 220 and entering the cavity 260 will not be coupled back into the return path of waveguide path 70, 74 and interfere with the main reflected signal from surface 235 of window 230.

Alternatively, cavity 260 can be filled with an epoxy cement that has an index of refraction matched to the waveguide 50. Cavity 260 is filled with an index matching epoxy that is initially uncured and liquid. Assembly 100 is then displaced toward and/or away from the waveguide 50 end 72 until an optimum focus of the image from the waveguide termination end 72 is made on outer surface 235 of window 230. Once the optimal focus is achieved, the assembly 200 is retained in this position and the epoxy filling cavity 260 is cured, thereby fixing assembly 200 at the focused position.

It will be appreciated by those skilled in the art that the present invention teaches the use of a variable gap for effectively gaining the maximum benefit from the focusing element's advantages in increasing the optical probe's field of view. The longitudinal displacement of the optical assembly 100, 200 allows the image of the waveguide end 72 to be transferred across cavity 160, 260 to the interface formed by outer surface 135, 235 and the suspension. The variable gap provided by cavity 160, 260 greatly reduces the complexity and precision of the elements utilized to complete the probe assembly.

The present invention has been described using an optical probe having an integrated optical surface waveguide 50. However, it will be appreciated by those skilled in the art that the embodiments of the present invention described herein can also be effectively practiced using optical probes having optical fibers, or optical fiber waveguides and, therefore, the present invention is not limited thereto.

The present invention has been described with particular reference to the preferred embodiments thereof. It will be obvious that various changes and modifications can be made therein without departing from the spirit and scope of the invention as defined in the appended claims.

What is claimed is:

1. A focusing assembly for an optical probe, said optical probe including a housing and an optical waveguide having a termination end for both the emission and reception of light images mounted within said housing with said termination end proximate a housing first end, said focusing assembly comprising:

a focusing element having a first and a second end mounted within a holder member, said holder member secured to said housing first end with said focusing element first end adjacent to and in contact with said optical waveguide termination end for both the emission and reception of light images by the focusing element;

a window having an inner and outer surface mounted on a body member with said window inner surface in a facing and spaced relationship to said focusing element second end; and said body member configured for being adjustably mounted to said holder member, for being adjusted to transfer and focus said light images from said focusing element second end and waveguide termination end to said window outer surface.

2. The focusing assembly for an optical probe as claimed in claim 1, wherein said body member includes a cowled portion extending from the periphery of said body member, said cowled portion arranged to engage and rest on an outer surface of said holder member, defining a cavity between said focusing element second end and said window inner surface whereby, responsive to the adjustment of said body member to focus said light images on said window outer surface, said cowled portion is displaced along said holder member, adjusting the size of said cavity.

3. The focusing assembly as claimed in claim 2 wherein said cavity is filed with air.

4. The focusing assembly as claimed in claim 3 wherein, responsive to the focus of said light images on said window outer surface, said cowled portion is fixed to said housing by applying and curing a fixing cement to said cowled portion and said holder member outer surface.

5. The focusing assembly as claimed in claim 2 wherein said cavity is filled with an epoxy material having an index of refraction that closely matches the index of refraction of said optical waveguide.

6. The focusing assembly as claimed in claim 5 wherein, responsive to the adjustment of said body member to focus said light images on said window outer surface, said cowled portion is fixed to said holder member by curing said index matching epoxy.

7. The focusing assembly as claimed in claim 2 wherein said holder member includes an opening extending longitudinally along said holder member and said focusing element is a GRIN rod fixedly retained within said opening.

8. The focusing assembly as claimed in claim 7 wherein said body member includes a front face having a recessed portion located on said front face, with said recessed portion open to said focusing element second end, whereby said window is mounted within said recess.

9. The focusing assembly as claimed in claim 8 wherein said window is composed of an optically transparent material.

10. The focusing assembly as claimed in claim 8 wherein said window is composed of an optically transparent glass material.

11. The focusing assembly as claimed in claim 8 wherein said window is composed of an optically transparent sapphire material.

12. A focusing assembly for an optical probe, said optical probe including a housing and an optical waveguide having a termination end for the emission and reception of light images mounted within said housing with said termination end proximate a housing first end, said focusing assembly comprising:

a focusing element having a first and a second end mounted within a body member;

a window having an inner and an outer surface mounted on said body member with said window inner surface resting against and in contact with said focusing element first end; and said body member being adjustably mounted to said housing first end with said focusing element second end in spatial and axial alignment with said optical waveguide termination end, for being adjusted to transfer said light images to said focusing element second end and to focus said light images on said window outer surface.

13. The focusing assembly for an optical probe as claimed in claim 12, wherein said means for adjustably mounting said body member to said housing includes a cowled portion extending from the periphery of said body member, said cowled portion arranged to engage said housing first end, defining a cavity between said termination end and said focusing element second end whereby, responsive to the adjustment of said body member to focus said light images on said window outer surface, said cowled portion is displaced along said housing, adjusting the size of said cavity.

14. The focusing assembly as claimed in claim 13 wherein said housing includes a receiving surface extending about the periphery of said housing first end, said receiving surface arranged to receive and adjustably accept thereon said cowled portion.

15. The focusing assembly as claimed in claim 14 wherein said cavity is filed with air.

16. The focusing assembly as claimed in claim 15 wherein, responsive to the focus of said light images on said window outer surface, said cowled portion is fixed to said housing by applying and curing a fixing cement to said cowled portion and said receiving surface.

17. The focusing assembly as claimed in claim 13 wherein said cavity is filled with an epoxy material having an index of refraction that closely matches the index of refraction of said optical waveguide.

18. The focusing assembly as claimed in claim 17 wherein, responsive to the adjustment of said body member to focus said light images on said window outer surface, said cowled portion is fixed to said housing by curing said index matching epoxy.

19. The focusing assembly as claimed in claim 13 wherein said body member includes an opening extending longitudinally along said body member and said focusing element is a GRIN rod fixedly retained within said opening.

20. The focusing assembly as claimed in claim 19 wherein said body member includes a front face having recessed portion located on said front face, with said recessed portion open to said focusing element first end whereby said window is mounted within said recess.

21. The focusing assembly as claimed in claim 20 wherein said window is composed of an optically transparent material.

22. The focusing assembly as claimed in claim 20 wherein said window is composed of an optically transparent glass material.

23. The focusing assembly as claimed in claim 20 wherein said window is composed of an optically transparent sapphire material.

24. A focusing assembly for an optical probe, said optical probe including an optical waveguide having a termination end for the emission and reception of light images, said focusing assembly comprising:

a light image receiving surface for receiving and projecting thereon light images;

a focusing element optically coupled to said optical waveguide termination end for receiving and projecting said light images, said focusing element located between said waveguide termination end and said light image receiving surface;

a body member securing the light image receiving surface, the body member configured for being movably mounted with respect to the waveguide for adjusting the positional location of said light image receiving surface, whereby the position of said light image receiving surface relative to the waveguide termination end is adjusted to a positional location where said light images are focused onto said light image receiving surface through said focusing element; and means for fixing said positional location.

* * * * *